United States Patent
Kubek

(10) Patent No.: US 11,273,077 B2
(45) Date of Patent: Mar. 15, 2022

(54) WOUND PACKING MATERIAL COMPRISING CHEMOEFFECTOR

(71) Applicant: CHEMOKIND, INC., Canaan, IN (US)

(72) Inventor: Edward W. Kubek, Canaan, IN (US)

( * ) Notice: Subject to any disclaimer, the term of this patent is extended or adjusted under 35 U.S.C. 154(b) by 0 days.

(21) Appl. No.: 15/569,353

(22) PCT Filed: Apr. 25, 2016

(86) PCT No.: PCT/US2016/029217
§ 371 (c)(1),
(2) Date: Oct. 25, 2017

(87) PCT Pub. No.: WO2016/176147
PCT Pub. Date: Nov. 3, 2016

(65) Prior Publication Data
US 2018/0296395 A1 Oct. 18, 2018

Related U.S. Application Data

(60) Provisional application No. 62/152,871, filed on Apr. 25, 2015, provisional application No. 62/240,838, filed on Oct. 13, 2015.

(51) Int. Cl.
| | | |
|---|---|---|
| *A61F 13/00* | (2006.01) | |
| *A61L 15/24* | (2006.01) | |
| *A61L 15/26* | (2006.01) | |
| *A61L 15/42* | (2006.01) | |
| *A61L 15/44* | (2006.01) | |
| *A61M 1/00* | (2006.01) | |
| *A61F 13/36* | (2006.01) | |
| *A61L 15/20* | (2006.01) | |
| *A61L 15/32* | (2006.01) | |

(52) U.S. Cl.
CPC .. *A61F 13/00063* (2013.01); *A61F 13/00068* (2013.01); *A61F 13/36* (2013.01); *A61L 15/20* (2013.01); *A61L 15/24* (2013.01); *A61L 15/26* (2013.01); *A61L 15/32* (2013.01); *A61L 15/42* (2013.01); *A61L 15/425* (2013.01); *A61L 15/44* (2013.01); *A61M 1/90* (2021.05); *A61L 2300/214* (2013.01); *A61L 2300/232* (2013.01); *A61L 2300/252* (2013.01)

(58) Field of Classification Search
CPC ............... A61F 13/00063; A61F 13/36; A61F 13/00068; A61L 15/42; A61L 15/32; A61L 15/20; A61L 15/24; A61L 15/44; A61L 15/425; A61L 15/26; A61L 2300/252; A61L 2300/214; A61L 2300/232; A61M 1/0088
See application file for complete search history.

(56) References Cited

U.S. PATENT DOCUMENTS

| | | | |
|---|---|---|---|
| 4,732,155 A | | 3/1988 | Zetter et al. |
| 2003/0069369 A1* | | 4/2003 | Belenkaya ........ A61F 13/00042 525/437 |
| 2004/0258698 A1* | | 12/2004 | Wightman ............. A61K 47/50 424/178.1 |
| 2009/0117168 A1 | | 5/2009 | Keenan |
| 2010/0159008 A1 | | 6/2010 | Barron et al. |
| 2012/0046589 A1 | | 2/2012 | Eckstein et al. |
| 2013/0150815 A1 | | 6/2013 | Luckemeyer et al. |
| 2014/0348780 A1 | | 11/2014 | Glasnapp |

FOREIGN PATENT DOCUMENTS

| | | |
|---|---|---|
| EP | 2366721 | 9/2011 |
| WO | WO 01/64258 | 9/2001 |
| WO | WO 2009/134967 | 11/2009 |
| WO | WO 2014/115124 | 7/2014 |

OTHER PUBLICATIONS

Odermatt et al. (EP2366721 (A1) English Translation) (Year: 2011).*
International Preliminary Report on Patentability for International (PCT) Patent Application No. PCT/EP2016/029217, dated Nov. 9, 2017 12 pages.
Kubek et al. "Negative-pressure wound therapy and the emerging role of incisional negative pressure wound therapy as prophylaxis against surgical site infections," Microbial pathogens and strategies for combating them: science, technology and education, FORMATEX, 2013, 1833-1846.
International Search Report for International Patent Application No. PCT/EP2016/029217, dated Jul. 27, 2016, 4 pages.
Written Opinion for International Patent Application No. PCT/EP2016/029217, dated Jul. 27, 2016, 8 pages.
Official Action for Canadian Patent Application No. 2983822, dated Sep. 25, 2018, 4 pages.
Extended European Search Report for European Patent Application No. 16786968.4, dated Dec. 11, 2018.
Official Action for Australian Patent Application No. 2016255417, dated Sep. 12, 2019, 4 pages.
Official Action for Canadian Patent Application No. 2983822, dated Jun. 17, 2020, 4 pages.
Official Action (English translation only) for Chinese Patent Application No. 201680032994.2, dated May 7, 2020, 13 pages.
Official Action for European Patent Application No. 16788968.4, dated Apr. 6, 2020, 7 pages.

* cited by examiner

*Primary Examiner* — Quanglong N Truong
(74) *Attorney, Agent, or Firm* — Sheridan Ross P.C.

(57) ABSTRACT

A wound packing material, particularly suitable for use in negative pressure wound therapy, comprising a porous material admixed with a chemoattractant. This disclosure further provides methods of manufacturing the wound packing material, and therapeutic methods of using the wound packing material.

15 Claims, 3 Drawing Sheets

DAY 1     DAY 2

INSIDE SURFACE

OUTSIDE SURFACE

Relative total bacterial burden
Pre-treatment/Post-treatment (A.U.)

0.67

DAY 1     DAY 2

INSIDE SURFACE

OUTSIDE SURFACE

Relative total bacterial burden
Pre-treatment/Post-treatment (A.U.)

7.1

WOUND PACKING MATERIAL COMPRISING CHEMOEFFECTOR

CROSS REFERENCE TO RELATED APPLICATIONS

This application is a national stage application under 35 U.S.C. 371 of PCT Application No. PCT/US2016/029217 having an international filing date of Apr. 25, 2016, which designated the United States, which PCT application claimed the benefit of U.S. Provisional Application Ser. No. 62/152,871, filed Apr. 25, 2015 and U.S. Provisional Application No. 62/240,838, filed Oct. 13, 2015, all of which are incorporated by reference in their entirety.

TECHNICAL FIELD

This disclosure relates generally to wound care. More specifically, this disclosure relates to wound packing elements for packing wound cavities (traumatic, surgical, and/or intentionally created for the purpose of therapy), particularly during negative pressure wound therapy.

BACKGROUND OF DISCLOSURE

Negative pressure wound therapy (NPWT) involves the application of a pressure that is reduced relative to that of the surroundings (i.e., "negative pressure") to a wound, thereby mechanically contracting the wound and removing fluids from the wound. This promotes the formation of granulation tissue and accelerates closure of the wound. The technique is particularly effective in the treatment of slow healing wounds such as chronic leg ulcers and large open wounds. In the general process of NPWT, a dressing consisting of an occlusive drape, traversed by a drainage tube, is applied to the wound opening, forming a seal under which a negative pressure can operate. The drainage tube is connected to a negative pressure source allowing the wound fluid to be drawn away. In the case of large open wounds, the wound cavity must be packed with a wound packing element to prevent the dressing from being drawn into the wound cavity by suction, and to ensure an even distribution of pressure throughout the wound.

These methods, and the materials and devices used in these methods are well known and described in applications disclosing specific wound treatment systems including, for example, U.S. Pat. No. 5,645,081, issued Jul. 8, 1997 and titled "APPARATUS FOR FACILITATING THE HEALING OF WOUNDS"; U.S. Pat. No. 7,964,766, issued Jun. 21, 2011 and titled "WOUND CLEANSING APPARATUS IN-SITU"; U.S. Pat. No. 8,715,256, issued May 6, 2014 and titled "VACUUM ASSISTED WOUND DRESSING"; U.S. Pat. No. 8,764,732 issued Jul. 1, 2014 and titled "WOUND DRESSING"; U.S. Pat. No. 8,808,274 issued Aug. 19, 2014, and titled "WOUND DRESSING"; U.S. Pat. Pub. No. 2011/0282309, filed Apr. 21, 2011 and titled "WOUND DRESSING AND METHOD OF USE." The entirety of these disclosures are hereby incorporated by reference. Additionally, devices for negative pressure wound therapy are commercially available, for example the V.A.C.™ device (Kinetic Concepts, Inc., San Antonio, Ill. 78265).

Wound packing elements used in these devices and methods should effectively fill a wound cavity, contacting the entire surface of the wound with substantially even pressure. The material is sufficiently compactable to enable contraction with the wound cavity when a negative pressure is applied, while also being firm enough to prevent the dressing from being drawn into the wound. The packing material permits free passage of fluid without becoming clogged to ensure an even distribution of pressure within the wound cavity, and is preferably non-adherent to the wound surface. Currently, wound packing elements consist of either gauzes or foams. The gauze type involves the use of a drain wrapped in gauze topped by a sealed dressing. Gauze is typically applied as a single layer, a drain is placed on the gauze and then a second piece of gauze is placed over the drain, creating a "gauze-sandwich". Gauze is most suitable as a packing element for smaller wounds and has a tendency to fragment upon redressing, which could potentially result in fibers remaining in the wound.

The foam type involves the use of foam placed over or in the wound. In foam based NPWT the wound cavity is filled or covered with a porous foam packing material and covered over and sealed with flexible sheet (a drape) that is fairly impermeable to fluids. A tube is inserted under or through the drape into the wound site and its distal end is connected to a vacuum source. The wound cavity, enclosed by the drape and tissue, contracts under the force of atmospheric pressure and compresses the packing material visibly. Gross tissue movement ceases after a few minutes and fluid is withdrawn from the wound. The fluid is transmitted through the packing material, up the vacuum tube to a collection receptacle. The wound packing material mechanically supports the tissue to which it is applied, and also allows the free flow of fluids away from the site when a vacuum is applied, even when compressed. A good material for this application is hydrophobic, reticulated polyurethane foam of very high free internal volume. The commercially available devices often use a wound dressing which contains an open-cell polymer foam such as polyvinyl alcohol (PVA) or polyurethane (PU). A range of foams with different properties are available, such as polyurethane foam (black) and polyvinyl-alcohol (PVA) (white) foam. PVA foam is denser and less permeable than polyurethane and requires a higher negative pressure to function effectively. The choice of foam depends on the application; for example, the more porous polyurethane foam is more commonly used on larger or deeper wounds. A combination of polyurethane and PVA foam can be used, depending on the desired result. Foam can be cut to fit the size and shape of the wound, and multiple pieces of foam may be used if necessary, although each piece of foam must come into contact with another piece of foam in order to achieve uniform compression when a negative pressure is applied. However, foams with sufficient density to effectively pack a wound often lack the required permeability and are often subject to clogging. The processes by which these polymeric foams are manufactured must be tightly controlled to avoid the introduction of unwanted agents into the material.

Variations and additions to these wound packing materials have been prepared. For example, British Patent 1417962 describes the use of a non-reticulated polyurethane foam which having a layer of collapsed cells, which facilitates the flow of moisture from the wound into the body of the foam material. A further refinement of such polyurethane foams, is described in PCT Publication No. WO 92/13576 and involves the addition of an alginate composition to the foam to raise the absorptive capacity of the foam and facilitates flow of moisture at a relatively high rate from very moist wounds. U.S. Pat. No. 3,903,232 discloses hydrophilic cross-linked polyurethane foams, useful for the absorption of body fluids and for external body cleaning, for internal body implant use, and as absorptive products such as diapers. European patent document EP-A-0335669 discloses a hydrophilic foam composition comprising the "in situ" reaction product of an isocyanate-capped polyether prepolymer, a hydrophilic agent capable of absorbing water, an adjuvant comprising an alcohol, a wetting agent and water. U.S. Pat. No. 4,728,323, describes methods of manufacturing a wound dressing which is comprised of a "substrate" coated with an antimicrobial film of a silver salt. Similarly, U.S. Pat. No. 4,997,425, provides a wound dressing which slowly releases antimicrobial compounds. U.S. Patent Publication No. 2002/0168400 provides a resin foam wound dressing having a collagen layer dispersed over the foam layer. U.S. Pat. No. 7,745,509, provides polymeric wound compositions with a metal oxide particles distributed within. U.S. Patent Publication No. 20140309574, provides gauze or knitted wound packing materials containing honey and/or silver. U.S. Patent Publication No. 2007/0161936 discloses open-cell foam dressings containing antimicrobial agents integrated into the dressing material. U.S. Pat. No. 8,772, 567 describes open-cell polyurethane foam dressings containing bovine serum to provide added tinsel strength to the dressing material.

These wound packing materials represent attempts to enhance the performance of wound dressings, particularly as used in NWPT methods. But the current choice of materials, is still limited, and no single packing material is ideal for all NPWT applications. For this reason, additional wound packing materials that may further enhance wound healing are desired.

The advantages and features of novelty characterizing aspects of this disclosure are pointed out with particularity in the appended claims. To gain an improved understanding of the advantages and features of novelty, however, reference may be made to the following descriptive matter that describe and illustrate various configurations and concepts related to the disclosure.

SUMMARY

This disclosure provides new forms of wound packing materials that depart significantly from the currently available wound packing materials, which contain antimicrobial agents. The wound packing materials of this disclosure are admixed with chemoeffector compounds that attract and foster the growth or sustain the metabolic activities of microorganisms. Thus, wound packing materials of this disclosure admixed with chemoattractant compounds are biologically-active symbiotic materials capable of removing microbes from the body without killing them. Without intending to be bound by theory, it is believed that these wound packing materials are highly nutritive, and microorganisms entering these materials may therefore down-regulate virulence factors. By determining a pathogen's unique metabolic and chemotactic preferences, the inventors can infuse targeted attractants into the wound packing materials with the therapeutic goal of removing pathogens by directed chemotaxis. This allows the clinician to adjust the environment so microorganisms transition freely toward a clinically desired phenotype beneficial to both host and the pathogen. Thus, the therapeutic use of the wound packing materials of this disclosure represents the opposite to the approach of using antibiotic therapy or wound packing materials containing antimicrobial compounds. The invention further provides methods of treating wounds using the novel wound packing materials of this disclosure.

The chemoeffectors admixed with the wound packing materials may be either chemoattractants or chemorepellents, binding proteins/receptors, or substances that simultaneously promote wound healing in the process of removing desired disease causing cells. Additionally, the chemoeffector(s) agents may be infused into wound packing materials during NPWT, thereby allowing various dwell times of the chemoeffector in the wound packing. Additionally, the chemoeffector agents may be admixed in a manner designed to allow slow diffusion of the chemoeffector agents onto the adjacent wound surface(s). Additionally, the chemoeffector agents may be applied underneath an NPWT wound packing material to establish chemoeffector gradients progressing to the wound surface and subsequently into the negative pressure wound packing material.

One preferred wound packing material comprises a dressing body having at least a wound contacting surface layer which is formed from a medically inert urethane open-cell foam. Preferably, the entire dressing body is formed of a hydrophilic polyurethane foam. However, there may be other polymer foams of the same general type, such as open-cell sponge rubber or foamed plastics, which can be impregnated with the active agents to be described, and which may become known to others skilled in the art of negative pressure wound therapy. Such open-cell polymer foams are included in the scope of this invention, as well as absorbent fiber materials.

The packing materials, dressings and methods of this disclosure are both simultaneously a wound-treatment, and a wound-dressing. Thus, these materials are not a medication or a pain reliever, and the dressing is not intended solely to "heal" a wound in every application. The wound care materials of this disclosure provide an environment within which the body's healing processes can proceed unimpeded, as particular toxic or infectious agents are drawn away from the wounded tissues, thereby allowing very rapid growth to the cellular layers in the wounded tissue. Infectious agents consume and thereby drain away regenerative fluids and proteins, excreting substances that may slow or retard healing. The healing is dramatically slowed because these substances are partially consumed by infectious microbes.

The wound care materials and methods of this disclosure remove infectious organisms by drawing them away from the infectious or infected tissue or infected surgical implant. In this way, these wound care materials maximize the speed at which tissue regeneration and therefore wound healing occurs, while simultaneously reducing or eliminating the need for antibiotic therapy.

The wound care materials and methods of this disclosure act to clean the wound site as infectious microorganisms present in or near the wound site are removed into the wound packing materials, which may be removed and replaced, thereby preventing the accumulation of such infection organisms within the wounded tissue.

The wound dressings of this disclosure may include an absorbent pad and an adhesive-coated film or fibrous woven material layer, but without any additional negative pressure therapy. Additionally, the methods of the invention are particularly useful for packing a wound cavity in the context of wound treatment using negative pressure wound therapy. Thus, in a further aspect of the disclosure, there is provided a method of negative pressure wound therapy, which comprises packing a wound cavity with one or more wound packing materials of this disclosure, followed by the application of reduced pressure to the wound cavity.

Thus, one aspect of this disclosure provides wound packing materials that are admixed or impregnated with at least one chemoeffector agent. In example embodiments, the chemoeffector agent is chemoattractant to a microorganism.

In other example embodiments, the chemoattractant agent is chemoattractant to a bacteria. In other example embodiments, the chemoattractant agent is specifically chemoattractant to human cells infected by viruses. n other embodiments, the chemoeffector agent is chemoattractant to at least one microorganism (planktonic or within a biofilm) selected from the group consisting of: *Acinetobacter* spp, *Burkholdaria cepacia*, *Campylobacter jejuni*, *Candida albicans* (binding proteins), *Candida glabrata* (binding proteins), *Entamoeba histolytica* (protozoan), *Plasmodium* spp, *Enterobacteria*, *Enterococcus* (VRE), *Escherichia coli* (multiple pathogenic strains), *Helicobacter pylori*, *Klebsiella pneumonia*, *Listeria monocytogenes*, *Mucormycosis*, *Mycobacterium tuberculosis*, *Pasturella* spp, *Propionibacterium acnes*, *Proteus mirabilis*, *Pseudomonas aeruginosa*, *Salmonella typhi, paratyphi*, *Serratia marcescens* and other *Serratia* spp, *Shigella* spp (*dysenteriae, flexneri, boydii, sonnei*), *Staphylococcus aureus* (CA MRSA, MRSA MSSA) and its biofilms, *Staphylococcus epidermidis*, *Staphylococcus lugdunensis*, *Staphylococcus saprophyticus*, *Streptococcus agalactiae*, *Streptococcus pneumonia*, *Streptococcus pyogenes*, and *Vibrio* spp.

In example embodiments, the chemoeffector agent is an amino acid, a peptide, a protein, a sugar, a mucin, a human milk oligosaccharide, a human selectin or adhesion molecule, a human cancer cell chemoattractant chemokine, and combinations thereof.

These agents may include carboxylic acids, aromatic compounds, biphenyl compounds, ethylenes, furans, dichloromethane, pyrimidines, and triazines.

In specific embodiments, the chemoeffector agent is selected from the group of quorum sensing autoinducers consisting of homoserine lactones and peptides N-(3-hydroxydodecanoyl)-L-homoserine lactone, N-Dodecanoyl-L-homoserine lactone, N-Dodecanoyl-L-homoserine lactone, N-Tetradecanoyl-L-homoserine lactone, N-(3-Oxotridecanoyl)-L-homoserine lactone, N-Hexanoyldecanoyl-L-homoserine lactone, *C. jejuni*, axenic culture medium, enzymatic hydrolysate of casein (Trypticase), N-acetylneuraminic acid from egg mucin, L-aspartate, L-serine, human intestinal mucus proteins, canine intestinal mucus proteins, porcine intestinal mucus proteins, quorum sensing autoinducer 2 (AI-2), α-Methyl-DL-aspartate (AMA), (±)-α-Amino-3-hydroxy-5-methyl-4-isoxazolepropionic acid (AMPA), formimino-L-aspartate (FIA), guanidinosuccinic acid (GSA), N-methyl-L-aspartate (NMA), N-formyl-L-aspartate (NFA), (2-Imino-4-oxo-thiazolidin-5-yl)-acetic acid (IOTA), cis-1,2-cyclohexane-dicarboxylic acid (CHDCA), phthalic acid (PA), cis-(2R,3S)-2,3-piperidine dicarboxylic acid (cis-PDA), L-malic acid (LMA), D-glucose, D-galactose, maltose, peptides, 3,4-dihydroxymandelic acid, pyrimidine, nucleic acids, amino acids, thymine, uracil, multivalent galactose derivatives, multivalent leucine ligands, ribose and D-ribose, L-arabinose, L-sorbose, leucine, tryptophan, valine, phenylalanine, indole, glycerol, tryptose, putrescine, cadaverine, and gamma-aminobutyrate (GABA), trichloroethylene, chloroform, L-fucose, D-galactose, N-acetyl-D-galactosamine, and N-acetyl-D-glucosamine, I-aspartate, mucin-like receptors, fibrinogen-like receptors, fibronectin-like receptors, GAG-like receptors, ferret airway mucus, human respiratory tract glycolipids, human salivary mucins, human nasal mucin, chitin oligosaccharides, Mucin Type O-glycans, secretory gel-forming mucins, MUC2, MUC5AC, MUC5B, MUC6, MUC7, MUC1, MUC3, MUC4, MUC12, MUC13, MUC17 Human Milk Oligosaccharides, Bovine Platelet Factor 4 (bPF4), Canine derived mucin protein, Porcine derived intestinal and gastric mucin, Bovine sub-maxillary mucin, bovine submaxillary mucin, bacterial LPS (lipopolysaccharide), bacterial chemotaxin, oxygen-generating compounds, CCL1, TCA3, I-309, CCL2, MCP-1, MCAF, JE, CCL3, MIP-1α, LD78α, CCL3L1, LD78β, CCL3P1, CCL3L2, CCL3L3, LD78β, CCL4, MIP-1β, CCL4L1, LAG-1, CCL4L2, LAG-1, CCL5, RANTES, CCL7, MCP-3, MARC, CCL8, MCP-2, CCL11, Eotaxin, CCL13, MCP-4, CCL14, HCC-1, CCL15, HCC-2, CCL16, HCC-4, LEC, CCL17, TARC, ABCD-2, CCL18, DC-CK-1, PARC, AMAC-1, CCL19, MIP-3β, ELC, Exodus-3, CCL20, MIP-3α, LARC, Exodus-1, CCL21, 6Ckine, SLC, Exodus-2, CCL22, MDC, STCP-1, AMCD-1, CCL23, CKβ8, MPIF-1, CCL24, Eotaxin-2, MPIF-2, CCL25, TECK, CCL26, Eotaxin-3, MIP-4α, IMAC, CCL27, CTACK, ILC, ESKINE, CCL28, MEC, CXCL1, GRO-α, MGSA-α, MIP-2, KC, p-CXCL1, CXCL1P, CXCL2, GRO-β, MGSA-β, MIP-2α, CXCL3, GRO-γ, MGSA-γ, MIP-2β, CXCL4, PF4, PF4, CXCL4L1, PF4V1, PF4-ALT, CXCL4V1, CXCL5, ENA-78, CXCL6, GCP-2, PPBP, NAP-2, beta-TG, CTAP-III, p-CXCL7, PPBPL1, CXCL8, IL-8, IL-8, CXCL9 MIG, CXC:10, CXCL10, IP10, CRG-2, CXCL11, I-TAC, CXCL12, SDF-1α, SDF-1β, SDF-1γ, CXCL13, BCA-1, BLC, CXCL14, BRAK, CXCL16, SR-PSOX, CXCL17, DMC, XCL1, Lymphotactin, SCM-1α, ATAC, XCL2, SCM-1β, CX3CL1, Fractalkine, Neurotactin, ABCD-3, MIF, Macrophage migration inhibitory factor, glycosylation-inhibiting factor, 656 Hex2Sia1, 657 Hex2Fuc2, 730 Hex3HexNAc1, 876 Hex3HexNAc1Fuc1, 1022 Hex3HexNAc1Fuc2, 1095 Hex4HexNAc2, 1241 Hex4HexNAc2Fuc1, 1387 Hex4HexNAc2Fuc2, 1533 Hex4HexNAc2Fuc3, E-selectin, L-selectin, P-selectin, VCAM1, ICAM-1, Mucosal vascular cell-adhesion molecule 1 (MADCAM1), neutrophil β2-integrins (CD11a/CD18 (LFA-1) and CD11b/CD18), Epidermal Growth Factor (EGF), CXCL12/CXCR4 (ligand/receptor), CCL21/CCR7 (ligand/receptor), ΔNP63α, CCR6-CCL20, and combinations thereof.

In some embodiments, the wound packing material comprises a foam. In example embodiments, the packing material comprises a polymer. In other example embodiments, the packing material comprises a gauze. In example embodiments, the wound packing material is an open-cell polymer selected from a polyvinyl alcohol (PVA) or a polyurethane (PU). The wound packing material may be any negative pressure wound therapy (NPWT) foam(s) on the market currently available, including bio-resorbable foams and less adhesive silicone foams.

Related aspects of this disclosure provide wound dressings. One embodiment provides a wound dressing for use in negative pressure wound therapy, the wound dressing comprising an occlusive backing layer fitted with a drainage port, and a wound packing material admixed or impregnated with at least one chemoeffector agent. In a specific embodiment, the chemoeffector agent in this wound dressing is selected from the chemoeffector agents listed above. Another embodiment provides a wound packing material including a dressing body having at least a wound contacting surface layer which is formed from a medically inert, moisture permeable, urethane open-cell foam. In this embodiment, the foam which makes up at least the wound contacting surface of the dressing body exists as a foam matrix comprised of interconnected foam cells with cell walls which has incorporated therein a chemoeffector agent incorporated into the foam matrix both topically on a foam cell surface and integrally within the foam cell wall. The wound packing material may be any negative pressure wound therapy (NPWT) foam(s) on the market currently available, including bio-resorbable foams and less adhesive silicone foams.

Another embodiments provides colloidal chemoattractant dressings for topical use (without negative pressure). In an example embodiment, these dressings are useful for treating wounds in a burn center. The design of this wound dressing comprises an adhesive, layered, colloidal dressing to be applied topically. Each successive layer of the colloidal dressing has a slightly higher concentration of a chemoattractant mixture designed to attract and remove the intended pathogen. For use in treating burns, for example in the case of use at a burn center, the layered colloidal chemoattractant dressing might have successive layers with increasing concentrations of amino acids to attract infectious microorganism, such as *Pseudomonas*. These layered dressings may be produced using 3D printing techniques, by printing successive layers of medical grade hydrocolloid impregnated with, for example, uniform nutrient suspension and increasing concentrations of amino acids. In example embodiments, the successive layers are 1 mm or 0.5 mm in thickness. The topical application of this dressing effectively lure pathogens, for example *Pseudomonas*, away from the patient/wound, and into the hydrocolloid dressing. Removing the dressing then removes the pathogen.

A related aspect of this disclosure provides negative pressure wound therapy (NPWT) devices containing any one of the packing materials of this disclosure. One embodiment provides a device for negative pressure wound therapy that includes a cover material for sealing a wound space; a connector for negative pressure source; and, a wound packing material admixed or impregnated with at least one chemoeffector agent.

Another aspect of this disclosure provides methods of treating a wound. One embodiment is a method for the treatment of a wound that includes providing a wound dressing comprising a wound packing material comprising at least one chemoeffector agent and a moisture vapor permeable cover layer; positioning the dressing over a wound site to form a sealed cavity over the wound site; and, applying negative pressure to the wound site so as to draw fluid from the wound site into the sealed cavity.

Another embodiment provides a method of negative pressure wound therapy including packing a wound cavity with one or more wound packing materials, and applying reduced pressure to the wound cavity, wherein the wound packing material is admixed or impregnated with at least one chemoeffector agent.

Another aspect of this disclosure provides methods of manufacturing a wound packing material. In one embodiment, a method of manufacturing a wound packing material includes providing a wound dressing body having at least a wound contacting surface layer which is formed from a medically inert, moisture permeable, urethane open-cell foam. In this embodiment, the foam which makes up at least the wound contacting surface of the dressing body exists as a foam matrix comprised of interconnected foam cells with cell walls which has incorporated therein a chemoeffector agent, and the active agent(s) are incorporated into the foam matrix both topically on a foam cell surface and integrally within the foam cell wall.

Another aspect of this disclosure provides a method of preparing a wound packing material by providing a wound packing material as set forth in this disclosure and removing portions of the wound packing material to shape the body of the material to substantially match the shape of a wound to be packed.

The disclosure also includes any combinations of these cited aspects.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

DESCRIPTION OF EMBODIMENTS

Figure 1:
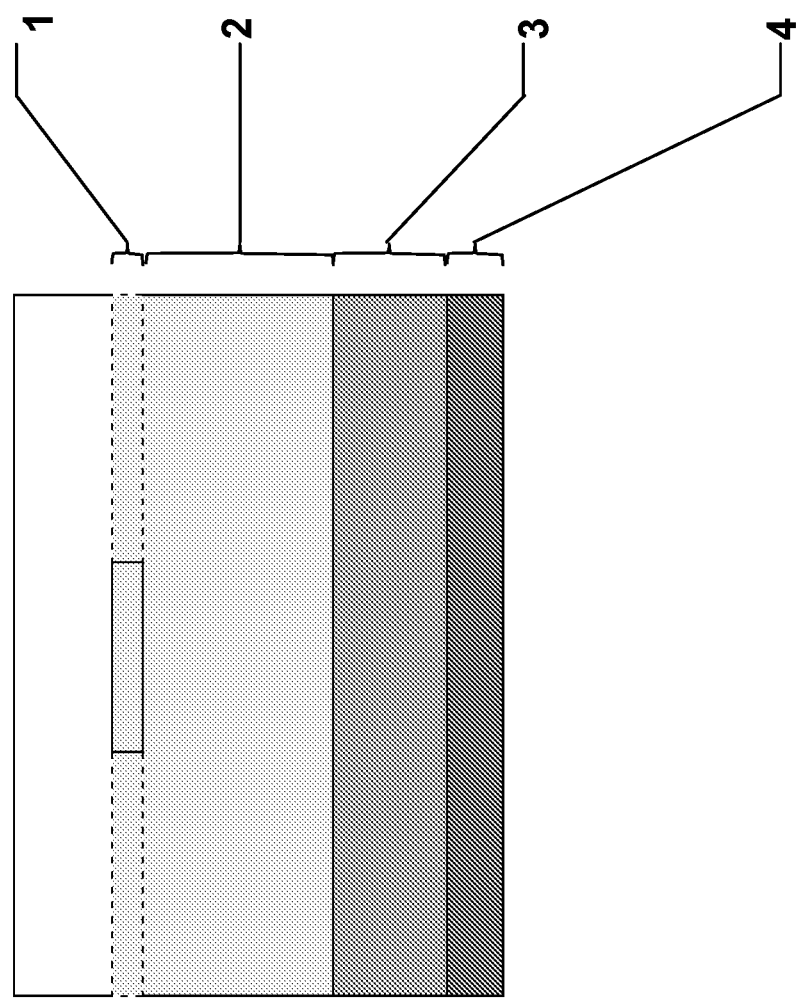
FIG. 1 shows a schematic of an in vitro layered system for testing chemoeffector compounds of this disclosure.

The present disclosure is drawn to wound packing materials and methods of using these materials in the treatment of wounds. These materials and methods enhance the healing processes by drawing infectious agents away from the wound, bloodstream, or infected surgical implant to speed wound healing and/or disease resolution.

A chemoattractant is generally understood to be a pharmacological agent which modulates the recruitment of cells. For example, white blood cells localize in body tissue where trauma has occurred as a result of attraction by chemicals secreted by the tissue surrounding the trauma. A chemoattractant used in the invention is preferably selected from the group consisting of N-(3-hydroxydodecanoyl)-L-homoserine lactone, N-Dodecanoyl-L-homoserine lactone, N-Dodecanoyl-L-homoserine lactone, N-Tetradecanoyl-L-homoserine lactone, N-(3-Oxotridecanoyl)-L-homoserine lactone, N-Hexanoyldecanoyl-L-homoserine lactone, *C. jejuni*, axenic culture medium, enzymatic hydrolysate of casein (Trypticase), N-acetylneuraminic acid from egg mucin, L-aspartate, L-serine, human intestinal mucus proteins, canine intestinal mucus proteins, porcine intestinal mucus proteins, quorum sensing autoinducer 2 (AI-2), α-Methyl-DL-aspartate (AMA), (±)-α-Amino-3-hydroxy-5-methyl-4-isoxazolepropionic acid (AMPA), formimino-L-aspartate (FIA), guanidinosuccinic acid (GSA), N-methyl-L-aspartate (NMA), N-formyl-L-aspartate (NFA), (2-Imino-4-oxo-thiazolidin-5-yl)-acetic acid (IOTA), cis-1,2-cyclohexane-dicarboxylic acid (CHDCA), phthalic acid (PA), cis-(2R,3S)-2,3-piperidine dicarboxylic acid (cis-PDA), L-malic acid (LMA), D-glucose, D-galactose, maltose, peptides, 3,4-dihydroxymandelic acid, pyrimidine, nucleic acids, amino acids, thymine, uracil, multivalent galactose derivatives, multivalent leucine ligands, ribose and D-ribose, L-arabinose, L-sorbose, leucine, tryptophan, valine, phenylalanine, indole, glycerol, tryptose, putrescine, cadaverine, and gamma-aminobutyrate (GABA), trichloroethylene, chloroform, L-fucose, D-galactose, N-acetyl-D-galactosamine, and N-acetyl-D-glucosamine, I-aspartate, mucin-like receptors, fibrinogen-like receptors, fibronectin-like receptors, GAG-like receptors, ferret airway mucus, human respiratory tract glycolipids, human salivary mucins, human nasal mucin, chitin oligosaccharides, Mucin Type O-glycans, secretory gel-forming mucins, MUC2, MUC5AC, MUC5B, MUC6, MUC7, MUC1, MUC3, MUC4, MUC12, MUC13, MUC17 Human Milk Oligosaccharides, Bovine Platelet Factor 4 (bPF4), Canine derived mucin protein, Porcine derived intestinal and gastric mucin, Bovine sub-maxillary mucin, bovine submaxillary mucin, bacterial LPS (lipopolysaccharide), bacterial chemotaxin, oxygen-generating compounds, CCL1, TCA3, I-309, CCL2, MCP-1, MCAF, JE, CCL3, MIP-1α, LD78α, CCL3L1, LD78β, CCL3P1, CCL3L2, CCL3L3, LD78β, CCL4, MIP-1β, CCL4L1, LAG-1, CCL4L2, LAG-1, CCL5, RANTES, CCL7, MCP-3, MARC, CCL8, MCP-2, CCL11, Eotaxin, CCL13, MCP-4, CCL14, HCC-1, CCL15, HCC-2, CCL16, HCC-4, LEC, CCL17, TARC, ABCD-2, CCL18, DC-CK-1, PARC, AMAC-1, CCL19, MIP-1β, ELC, Exodus-3, CCL20, MIP-3α, LARC, Exodus-1, CCL21, 6Ckine, SLC, Exodus-2, CCL22, MDC, STCP-1, AMCD-1, CCL23, CKβ8, MPIF-1, CCL24, Eotaxin-2, MPIF-2, CCL25, TECK, CCL26, Eotaxin-3, MIP-4α, IMAC, CCL27, CTACK, ILC, ESKINE, CCL28, MEC, CXCL1, GRO-α, MGSA-α, MIP-2, KC, p-CXCL1, CXCL1P, CXCL2, GRO-β, MGSA-β, MIP-2α, CXCL3, GRO-γ, MGSA-γ, MIP-2β, CXCL4, PF4, PF4, CXCL4L1, PF4V1, PF4-ALT, CXCL4V1, CXCL5, ENA-78, CXCL6, GCP-2, PPBP, NAP-2, beta-TG, CTAP-III, p-CXCL7, PPBPL1, CXCL8, IL-8, IL-8, CXCL9 MIG, CXC:10, CXCL10, IP10, CRG-2, CXCL11, I-TAC, CXCL12, SDF-1α, SDF-1β, SDF-1γ, CXCL13, BCA-1, BLC, CXCL14, BRAK, CXCL16, SR-PSOX, CXCL17, DMC, XCL1, Lymphotactin, SCM-1α, ATAC, XCL2, SCM-1β, CX3CL1, Fractalkine, Neurotactin, ABCD-3, MIF, Macrophage migration inhibitory factor, glycosylation-inhibiting factor, 656 Hex2Sia1, 657 Hex2Fuc2, 730 Hex3HexNAc1, 876 Hex3HexNAc1Fuc1, 1022 Hex3HexNAc1Fuc2, 1095 Hex4HexNAc2, 1241 Hex4HexNAc2Fuc1, 1387 Hex4HexNAc2Fuc2, 1533 Hex4HexNAc2Fuc3, E-selectin, L-selectin, P-selectin, VCAM1, ICAM-1, Mucosal vascular cell-adhesion molecule 1 (MADCAM1), neutrophil β2-integrins (CD11a/CD18 (LFA-1) and CD11b/CD18), Epidermal Growth Factor (EGF), CXCL12/CXCR4 (ligand/receptor), CCL21/CCR7 (ligand/receptor), ΔNP63α, CCR6-CCL20, and combinations thereof.

The wound packing materials of this disclosure may include open-cell polyurethane foam(s). Such foams are usually materials with cells (open, closed, or both) distributed over their whole mass. Such materials thus usually have a raw density (in accordance with DIN EN ISO 845), which is lower than the density of the basic substance. A cell is an individual cavity formed in the manufacture of the foam which is partially or fully enclosed by the cell walls and/or cell struts. A closed cell is usually a cell which is completely enclosed by its walls and has no connection via the gas phase with the other cells. An open cell is usually a cell which is connected with other cells via the gas phase. In the context of this application, the term open-cell means that in the polyurethane foam there is at least 60% open cells, preferably at least 90% open cells, even more preferably 98% open cells, in particular essentially 100% open cells relative to the total number of cells. The open cell content of the polyurethane foam is usually determined in accordance with ASTM D 2856-87, procedure B. Preferably, the open-cell polyurethane foam(s) that may form parts of the packing materials of this disclosure are impregnated or coated with chemoeffector substances.

Applying or achieving negative pressure in the wound space in the context of this disclosure describes an air pressure which is lower inside the wound dressing or a wound cavity compared to the atmospheric pressure. "Within the wound dressing" refers to the cavity formed between the cover material and the wound.

Wound packing materials of this disclosure may include any of the commonly known wound packing materials, including foam or gauze or combinations thereof, or obvious variations of these materials to be discovered, admixed with at least one chemoeffector agent. By admixed, it is meant that the chemoeffector agent is impregnated into the wound packing material and/or applied to a surface of the wound packing material or both impregnated into and applied to a surface of the wound packing material.

Chemoeffector agent(s) are usually admixed with the wound packing material in a quantity of 0.01 to 30 weight percent, preferably from 0.1 to 15 weight percent, relative to the total weight of the wound packing material.

For certain wound packing compositions of this disclosure, having, for example, a volume of about 100 ml, the amount of chemoeffector admixed in the composition may range from about 1 ng to about 500 g, preferably from about 100 ng to 100 mg, depending on the chemoeffector used.

The pH of the wound packing materials of this disclosure is preferably from about pH 6 to about pH 8. More preferably it is about pH 6.7 to about pH 7.2. In certain embodiments, the wound packing materials of this disclosure may be admixed with pH modifying agents to create a pH gradient extending away from the surface of the wound tissue into the wound packing material. In this configuration, the pH gradient is the chemoattractant within the wound packing material, as certain microorganisms are attracted to an environment of specific pH. In specific embodiments, the pH gradient may be either acidic or basic at or near the surface of the wound packing material that is in contact with the tissue of the wound and the pH gradient extends to a neutral pH of about pH 7 within regions of the wound packing materials that are distant to the surface of the material that is in contact with the tissue, in order to attract microorganisms that are drawn from either acidic or basic environments to a neutral pH.

The chemoeffector compounds admixed with the wound packing materials may be either binding proteins, receptors, antibodies, chemoattractants or chemorepellents (collectively known as "chemoeffectors").

Chemoattractant compounds may include all 20 amino acids, peptides, proteins, sugars, mucins, human milk oligosaccharides, human selectins or adhesion molecules, growth factors, human cancer cell chemoattractant chemokines, and combinations thereof.

Chemorepellents may include specific amino acids, Leucine, Tryptophan, Valine, Phenylalanine, Indole, Glycerol, or any of the previously mentioned chemoeffectors as attractants for one target may act as repellents for another.

Specific chemo effectors may include N-(3-hydroxydodecanoyl)-L-homoserine lactone, N-Dodecanoyl-L-homoserine lactone, N-Dodecanoyl-L-homoserine lactone, N-Tetradecanoyl-L-homoserine lactone, N-(3-Oxotridecanoyl)-L-homoserine lactone, N-Hexanoyldecanoyl-L-homoserine lactone, C. jejuni, axenic culture medium, enzymatic hydrolysate of casein (Trypticase), N-acetylneuraminic acid from egg mucin, L-aspartate, L-serine, human intestinal mucus proteins, canine intestinal mucus proteins, porcine intestinal mucus proteins, quorum sensing autoinducer 2 (AI-2), α-Methyl-DL-aspartate (AMA), (±)-α-Amino-3-hydroxy-5-methyl-4-isoxazolepropionic acid (AMPA), formimino-L-aspartate (FIA), guanidinosuccinic acid (GSA), N-methyl-L-aspartate (NMA), N-formyl-L-aspartate (NFA), (2-Imino-4-oxo-thiazolidin-5-yl)-acetic acid (IOTA), cis-1,2-cyclohexane-dicarboxylic acid (CHDCA), phthalic acid (PA), cis-(2R,3S)-2,3-piperidine dicarboxylic acid (cis-PDA), L-malic acid (LMA), D-glucose, D-galactose, maltose, peptides, 3,4-dihydroxymandelic acid, pyrimidine, nucleic acids, amino acids, thymine, uracil, multivalent galactose derivatives, multivalent leucine ligands, ribose and D-ribose, L-arabinose, L-sorbose, leucine, tryptophan, valine, phenylalanine, indole, glycerol, tryptose, putrescine, cadaverine, and gamma-aminobutyrate (GABA), trichloroethylene, chloroform, L-fucose, D-galactose, N-acetyl-D-galactosamine, and N-acetyl-D-glucosamine, I-aspartate, mucin-like receptors, fibrinogen-like receptors, fibronectin-like receptors, GAG-like receptors, ferret airway mucus, human respiratory tract glycolipids, human salivary mucins, human nasal mucin, chitin oligosaccharides, Mucin Type O-glycans, secretory gel-forming mucins, MUC2, MUC5AC, MUC5B, MUC6, MUC7, MUC1, MUC3, MUC4, MUC12, MUC13, MUC17 Human Milk Oligosaccharides, Bovine Platelet Factor 4 (bPF4), Canine derived mucin protein, Porcine derived intestinal and gastric mucin, Bovine sub-maxillary mucin, bovine submaxillary mucin, bacterial LPS (lipopolysaccharide), bacterial chemotaxin, oxygen-generating compounds, CCL1, TCA3, I-309, CCL2, MCP-1, MCAF, JE, CCL3, MIP-1α, LD78α, CCL3L1, LD78β, CCL3P1, CCL3L2, CCL3L3, LD78β, CCL4, MIP-1β, CCL4L1, LAG-1, CCL4L2, LAG-1, CCL5, RANTES, CCL7, MCP-3, MARC, CCL8, MCP-2, CCL11, Eotaxin, CCL13, MCP-4, CCL14, HCC-1, CCL15, HCC-2, CCL16, HCC-4, LEC, CCL17, TARC, ABCD-2, CCL18, DC-CK-1, PARC, AMAC-1, CCL19, MIP-1β, ELC, Exodus-3, CCL20, MIP-3α, LARC, Exodus-1, CCL21, 6Ckine, SLC, Exodus-2, CCL22, MDC, STCP-1, AMCD-1, CCL23, CKβ8, MPIF-1, CCL24, Eotaxin-2, MPIF-2, CCL25, TECK, CCL26, Eotaxin-3, MIP-4α, IMAC, CCL27, CTACK, ILC, ESKINE, CCL28, MEC, CXCL1, GRO-α, MGSA-α, MIP-2, KC, p-CXCL1, CXCL1P, CXCL2, GRO-β, MGSA-β, MIP-2α, CXCL3, GRO-γ, MGSA-γ, MIP-2β, CXCL4, PF4, PF4, CXCL4L1, PF4V1, PF4-ALT, CXCL4V1, CXCL5, ENA-78, CXCL6, GCP-2, PPBP, NAP-2, beta-TG, CTAP-III, p-CXCL7, PPBPL1, CXCL8, IL-8, IL-8, CXCL9 MIG, CXC:10, CXCL10, IP10, CRG-2, CXCL11, 1-TAC, CXCL12, SDF-1α, SDF-1β, SDF-1γ, CXCL13, BCA-1, BLC, CXCL14, BRAK, CXCL16, SR-PSOX, CXCL17, DMC, XCL1, Lymphotactin, SCM-1α, ATAC, XCL2, SCM-1β, CX3CL1, Fractalkine, Neurotactin, ABCD-3, MIF, Macrophage migration inhibitory factor, glycosylation-inhibiting factor, 656 Hex2Sia1, 657 Hex2Fuc2, 730 Hex3HexNAc1, 876 Hex3HexNAc1Fuc1, 1022 Hex3HexNAc1Fuc2, 1095 Hex4HexNAc2, 1241 Hex4HexNAc2Fuc1, 1387 Hex4HexNAc2Fuc2, 1533 Hex4HexNAc2Fuc3, E-selectin, L-selectin, P-selectin, VCAM1, ICAM-1, Mucosal vascular cell-adhesion molecule 1 (MADCAM1), neutrophil β2-integrins (CD11a/CD18 (LFA-1) and CD11b/CD18), Epidermal Growth Factor (EGF), CXCL12/CXCR4 (ligand/receptor), CCL21/CCR7 (ligand/receptor), ΔNP63α, CCR6-CCL20, and combinations thereof.

This disclosure also provides wound dressings, which are composed of the wound packing materials of this disclosure fitted with materials specifically for use with negative pressure wound therapy. This includes for example and occlusive backing layer applied to at least one surface of the wound packing material. This may also include a drainage port and/or tubing to be connected to a source of negative pressure. In specific embodiments, the wound packing material comprises a urethane open cell foam having at least one surface adhered to the occlusive backing layer. In specific embodiments, the occlusive backing layer is applied to the planar surface of the foam in a pre-packaged manner. In specific embodiments, the occlusive backing layer is applied by the caregiver after the foam is shaped and placed in the wound.

This disclosure also provides negative pressure wound therapy devices which contain at least one wound packing material of this disclosure. These devices include, in addition to a wound packing material and mixed with one chemoeffector of this disclosure, a cover material for sealing the wound space, and a connector (i.e., a port and/or tubing) for a negative pressure source.

This disclosure also provides methods of using the wound packing materials of this disclosure. These methods generally include the application or placement of a wound packing material, bioresorbable or non-bioresorbable, of this disclosure in contact with a wound cavity or an internal cavity (i.e., implantation of the wound packing material into a body of a mammal) in order to draw an undesirable agent (i.e., an infectious microorganism, or a cancer cell) from the contacting mammalian tissue into the wound packing material. The methods specific to negative pressure wound therapy include positioning a wound dressing of this disclosure into and/or over a wound site to form a sealed cavity over the site, and applying negative pressure to the wound site to draw fluid from the wound site into the wound packing material in the sealed cavity. Commonly, in the use of these wound packing materials, the materials are shaped to closely match the contours of the wound cavity. This shaping may include cutting, ripping, shearing, or otherwise molding the wound packing material to match the shape of the interior cavity of the wound. This shaping is particularly useful when deploying the wound packing materials of the present disclosure in negative pressure wound therapy techniques.

In certain embodiments, the wound packing materials of this disclosure are deployed or implanted at wound sites within the body of a mammal. This may be, for example at a surgical site, and the wound packing materials may be implanted at the site at the time of a surgery by the surgeon in order to attract an infectious microorganism, or a cancer cell, or the like that may be present within or near the surgical site into the packing material. In specific embodiments, these wound packing materials may be deployed within a silastic structure that retains the wound packing materials but is perforated in one or more places to allow contact between the wound packing material and the surrounding mammalian tissue. In these embodiments, the silastic structure is preferably substantially in the shape of a sphere that may range in diameter from about 0.5 cm to about 20 cm. In these embodiments, multiple silastic structures containing the wound packing materials may be deployed by the surgeon. Additionally, multiple silastic structures containing the wound packing materials may be connected, either directly or by cords or the like, in order to make their retrieval relatively easy at a time when the surgeon determines they should be removed from the implant site.

In another aspect, the wound packing materials of this disclosure may be placed in contact with a surgical site by the placement of surgical drain tube (for example a drain tube used in a Jackson-Pratt drain, or similar surgical drain tubing) containing the wound packing materials within the surgical site. In example embodiments, the surgical drain tubing includes at least a portion of the tube comprising the wound packing material such that the placement of the tubing places the wound packing material within the surgical site in order to attract an infectious microorganism, or a cancer cell, or the like, that may be present within or near the surgical site into the packing material. The distal end of the drain tube comprising the wound packing material is then connected to a source of negative pressure to drain liquid from the surgical site.

In example embodiments, this modified and enhanced Jackson-Pratt drain would include a typical 10 French or larger diameter soft surgical tube with multiple holes or channels at the distal end, consistent with a typical surgical drain. However, the drain tubing employed in these embodiments would have a smaller, inner channel to allow for bi-directional flow. The larger suction channel would have a core comprised of reticulated open-cell black foam at the distal end, similar to the black foam commonly used in negative pressure wound therapy (NPWT). The much smaller (typically about 1.5 mm diameter) inner channel would be a forward flow channel (i.e., toward the patient). This inner "forward flow" channel would be used to infuse the chemoattractant. Once infused in the area proximate the foam, the larger negative pressure (suction) channel containing the black NPWT foam would remove the attractant and bathe the foam as it was removed. In this way, a negative pressure source, such as a bulb or small NPWT pump, would be used to apply negative pressure. Whether timed with a small electric or battery operated pump to include a dwell time, or rate matched with a compressing (forward flow) and expanding (negative pressure) bulb, this system constantly instills and removes chemoattractant from the surgical site.

In related embodiments, the surgical drain tube may be bi-directional tubing similar to the surgical drain tubing described above, which includes at least a portion of the tube comprising a wound packing material of this disclosure, and an additional, narrower tube located interior to the drain tubing. Chemoeffector compounds of this disclosure may be deployed through the narrower, interior tubing to the wound packing material in the wider, exterior surgical drain tube. In this way, the surgical drain tubing is "bi-directional" and the chemoeffector compound(s) present in the wound packing material may be replenished while the surgical drain tube remains in position in contact with the surgical site on one end and in contact with a source of negative pressure on the opposite end. This also allows the chemoeffector compound(s) present in the wound packing material to be replaced or changed while the surgical drain tube remains in contact with the surgical site. This disclosure also provides methods of manufacturing the wound packing material for the present disclosure. These methods include preparing and providing a sterile wound packing material including any of the commonly known wound packing materials, such as a foam or gauze or combinations thereof, or obvious variations of these materials to be discovered, and admixing the wound packing material with at least one chemoeffector agent of this disclosure. The chemoeffector agent may be applied to the wound packing material by spraying the packing material with a composition containing the chemo effector agent, or by soaking the wound packing material in a solution containing the chemo effector agent. Alternatively or additionally, the chemo effector agent may be chemically bound to the packing material through, for example, covalent or ionic bonds.

Additionally, this disclosure provides kits comprising components for use in negative pressure wound therapy, including the wound packing materials in accordance with the present invention, whereby the wound packing material may be impregnated with and/or coated with a chemoeffector compound of this disclosure, or the chemoeffector compound may be provided separately from the wound packing material.

Thus, in one embodiment, the kit for negative pressure wound therapy includes a cover material for forming a seal over the wound space, i.e. the wound cavity and an area surrounding the wound, a suitable means for connecting a negative pressure source (preferably a means for the functional connection of the wound space with a negative pressure source outside of the cover material in such a way that a negative pressure can be generated in the wound space and fluids can be drawn out of the wound space by suction), a wound packing material, and at least one chemoeffector compound of this disclosure, which is impregnated into or coated onto or separately stored from the wound packing material. In certain embodiments, the wound packing material in these kits comprises an open-cell polyurethane foam. In certain embodiments, the wound packing material included the kit is provided in a water-proof pack and in a sterile form. In related embodiments, the pack containing the kit components is provided in a form whereby radiation and/or ethylene oxide can be used for sterilization. These kits may contain further optional elements such as adhesive means to fix wound dressings to skin or other tissues, sealing means to generate an air-tight seal of wound dressings, pressure sensors, connection elements for pressure sensors, additional tubes, connectors for tubes, disinfectants, skin care products, or instructions for use. The kit may optionally contain scissors, pads and/or pincers, in particular in sterile form. The kit may also contain a ready-to-use negative pressure unit.

Another embodiment of the disclosure relates to the use of any of the wound packing materials described herein in the preparation of a treatment of a wound.

Each publication or patent cited herein is incorporated herein by reference in its entirety. The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1

This approach can be used to demonstrate if chemotaxis of bacteria from a reservoir (the "bacteria layer") to the vac foam is enhanced in the presence of an infused chemoattractant or presence of a chemorepellent. Referring to FIG. 1, the experimental system is constructed when layers are assembled in a clear vessel (to allow imaging) with a flat bottom. May be constructed in a flat bottomed tube, or a 50 mL conical tube if the conical portion of the tube is filled in with normal agar.

Target layer (1): Sponge, either laying on top of travel layer alone, or embedded in a layer of minimal swim agar. The embedding could be important for keeping the foam from drying out and to produce a close contact with the "travel layer."

Travel layer (2). Minimal swim agar (0.2%). This is where chemotaxing bacteria can be observed.

Bacteria layer (3). Bacteria are suspended in cooled, but molten minimal swim agar. Overnight culture in LB rinsed in M9 buffer and added directly.

Optional Repellent layer (4). This layer can contain a repellent that will diffuse into the above layers. The "repellent layer" is normal minimal agar (may be poured the night before). The other layers have to be built subsequently at the time of the experiment.

The agar will be prepared as follows:

| Minimal medium for PA (normal agar) | | |
|---|---|---|
| Ingredient | 1 L | 500 ml |
| Distilled water | 985 ml | 492.5 ml |
| Glycerol | 15 ml | 7.5 ml |
| LDGlutamine | 5 g | 2.5 g |
| $K_2HPO_4$ | 1.5 g | 0.75 g |
| MgSO4 | 0.2 g | 0.1 g |
| Agar | 15 g | 7.5 g |
| Adjust pH to 7.0, autoclave and cool. | | |

Example 2

To address whether the addition of a chemoattractant to the vac foam will elicit chemotaxis, no repellent is used. Referring to FIG. 1, a chemoattractant added to the sponge. Chemotaxis is monitored visually. Luminescent bacteria may be used to obtain better pictures, but wild type bacteria should be visible. For data collection, images are taken at a time interval that is optimized empirically. At the end of the experiment, the relative bacterial load on the sponge may be measured either via luminescence or by plating. Control values are obtained using the same set up without added chemoattractant.

Chemoattractant Mixture:

The following are mixed to give the final concentrations indicated:

L-amino acids (10 mM arginine; asparagine; glutamine; leucine; serine)
Bovine mucin (100 µg/mL)
OPTIONAL: D-galactose (≤0.1M)**

**D-galactose is a favorable carbon source, so it could support additional proliferation, but it is a strong attractant.

Example 3

Purpose: to address whether the addition of a repellent to the system will accelerate chemotaxis to vac foam. Referring to FIG. 1, a chemoattractant added to the sponge. Chemotaxis is monitored visually. Luminescent bacteria may be used to obtain better pictures, but wild type bacteria should be visible. For data collection, images are taken at a time interval that is optimized empirically. At the end of the experiment, the relative bacterial load on the sponge may be measured either via luminescence or by plating. Control values are obtained using the same set up without added chemorepellent.

Chemorepellent mixture (Final concentrations are given):

trichloroethylene (0.5 mg/mL)
chloroform (15 mg/L)
methyltiocyanate (100 mg/L)
DL-trifluoroleucine

Example 4

The animal study of chemoattractants used for in vivo testing of a chemoattractant infused into a vac dressing.

Protocol Overview:

1) Mice are weighed, and administered (anesthesia by the Isoflurane (up to 3% via nose cone), and receive a full thickness cutaneous injury (1.2 cm biopsy removed), from the lower back. Saline was administered IP, 0.5-0.8 ml one time, after the skin removal, and Buprenorphine (0.05-0.1 mg/kg s.c. q.12 hours, as needed)

2) *Pseudomonas aeruginosa* expressing luciferase were administered to the wound and the infection allowed to progress for 12 hours or 24 hours. A mesh piece (1 cm diameter) was placed over the wound after bacterial infection. Immediately after bacterial inoculation, IVIS image after covering the infected wound/wound edge/back with tegadem. IVIS imaging in two groups of animals matched with controls after 12 and 24 hours inoculation, before starting the treatment/connection to the V.A.C.

3) A premade, gas-sterilized dressing (ring, sponge, and two tubes) was placed over the wound, and secured to the skin (edge of the wound) by double-sided adhesive tape. The mouse was removed from the IVIS machine to the single housing modified cage, and the tubes of the dressing were connected to the VAC and pump. Wound treatment will be applied using negative pressure therapy (150 mmHg) and standard black GranuFoam™ directly over the wound (about 1.5 cm diameter/same size of the internal diameter of the ring) according to schedule of 5 minutes on, 1 minute off at intensity setting of 5.

4) Chemoattractants (L-amino acid cocktail containing arginine, asparagine, glutamine, leucine, serine, bovine mucin, and optionally D-galactose) and/or control solutions (0.9% saline) were infused into the dressing and then remained (treatment solution or saline in 10/60 ml syringe installed on the pump) for a dwell time of 1 minute before negative pressure resumed according to schedule synced.

5) Wound therapy consists of a repeating cycle as follows: active negative pressure wound therapy is initiated, negative pressure pauses, chemoattractant infused into GranuFoam™, pause continues to allow dwell time for chemoattractant, negative pressure resumes, negative pressure pauses, cycle repeats continuously. No mechanical wound debridement is performed at any time. Ring/dressing sponge was collapsed at all times under the vac negative presser; i.e., no air/fluid leaking.

6) 24 Hours after starting the treatment/connecting to VAC, the VAC/Pump was disconnected, and the dressing removed carefully to avoid surrounding contamination. The animal, and wound area and the sponge (inside and outside surface) were imaged using IVIS Imaging. (During IVIS imaging animals were anesthetized using isoflurane by up to 3% via nose cone). While the animal was under isoflurane anesthesia, the following tissues were collected: wound tissue (muscle), skin from the edge of the wound, and spleen, and placed on ice immediately.

7) T animals were sacrificed by opening the chest cardiac puncture, collecting the blood with heparinized syringe, and placed on ice immediately.

Bacterial Culturing:

The *Pseudomonas aeruginosa*—Xen41 was received as a frozen stock, seeded in 15 mL conical tubes with 4 mL of HB broth, grown for 2-4 hours until OD reached about 0.2. 500 uL was then taken from these tubes and seeded in 4 mL and grown until OD was 0.8-1 (exponential phase).

Wound Dressings and Vacuum System 24 hours after the infection, the mice were imaged to visualize the status of the infection. After imaging, vacuum treatment is initiated. With the mouse under anesthesia, the wound dressing was applied. The dressing consisted of a 5/8" rubber gasket. The gasket had two holes drilled through the side walls, allowing for two PE90 catheter tubes to be inserted. The inner wall of the gasket was beveled at approximately 45-degree angle along the top surface, all the way down to the bottom surface. On the bottom of the gasket, double sided medical grade tape was applied to adhere the gasket to the tissue surface. On the top surface of the gasket, a wound vac dressing drape is applied. The catheter tubing was inserted into the two pre-drilled holes, with the shorter tube being the vacuum tube, and the longer tube being the infusion tube. They were placed approximately on opposite sides of the gasket, with the vacuum tube positioned closer to the tail of the animal. GranuFoam™ cut in a circle to match the gasket opening, and 1.5 cm thick was centered in the gasket opening. It was held in place by the drape adhesive, and the catheter tubing was embedded within the foam, near the top side of the foam (about ¼ the way down from the top). The entire assembly was gas sterilized before use.

A VAC freedom system designed for veterinary use was used to apply a constant vacuum pressure (up to 200 mmHg). Initially, a constant pressure of about 150 mmHg, 24 hrs/day was used except during infusion and imaging or other procedures. The pump was turned off for approximately 1 minute every 6 minutes (5 minutes on, 1 minute off cycle), during which the chemoattractant solution was infused into the wound dressing.

Chemoattractant cocktail(s) or control solutions were infused and may include any of the following chemoattractants at concentrations determined in in vitro experiments: a) any of 20 L-amino acids, b) Intermediates of amino acid metabolism: putrescine, cadaverine, and gamma-aminobutyrate (GABA), c) human MUC1 or porcine gastric mucin, d) L-fucose, D-galactose, N-acetyl-D-galactosamine, N-acetyl-D-glucosamine, glucose, or succinate.

IVIS Spectrum Imaging:

Mice are imaged beginning 24 h after the initial infection, continuing up to 7 days post-infection. The time interval of imaging will be 6, 12, 24 hours, and adjustments as needed.

1. Under isoflurane anesthesia (up to 3% via nose cone), wound dressings were removed and the wound tissue/surface was otherwise left undisturbed; i.e., no irrigation or mechanical debridement was performed to reduce work during dressing changes.

2. Animals were placed in the IVIS Spectrum imager, and an image was acquired to quantify bacterial burden.

3. The dressing sponge was also imaged for determination of bacterial burden. The tissue proximal side is the most relevant.

4. Wound dressings were reapplied and the vacuum system was reconnected to apply negative pressure 5. Animals were also weighed daily during this procedure and observations of animal mobility and general appearance were recorded.

Study End:

Day 3 after wound procedure, or when the animal becomes moribund, the animal was euthanized using $CO_2$ or isoflurane inhalation. Tissue was collected from the skin edge and center and muscle underlying the wound, as well as a distal skin sample. The spleen was recovered and stored. Serum was also collected and stored. Tissue biopsies were transferred on ice from GHRB in triple containment (a Falcon tube inside 50 mL conical placed within a sealed plastic bag). The tissue was weighed immediately, prepped and mechanically homogenized in an equal volume of 0.9% saline. The homogenates were then serially diluted and plated. The serial dilutions were done in at least triplicate to minimize the contribution of pipetting error. The dilutions were plated for CFUs in the sponge and frozen bacteria in 1 mL of Trizol. After 18-24 hours, the colonies were counted. The plates were imaged for record keeping and to verify that the bacteria were luminescent.

Infusion and Vacuum Setup

The KCI freedom system was used to apply the vacuum pressure with adapters used to deliver the vacuum to the mouse using PE90 tubing (BTPE90, Instech Labs). One or more Y-Splitters (KCI) were used to deliver vacuum to multiple animals. A cap was placed on the first Y-splitter, since the sensing channels are applied to the first path only using the KCI splitter, this causes the sensing channel to report based on the main line pressure. A one way check valve was used to prevent backflow during the vac off cycle, and then connected to a 3/16" ID tubing (ST25, Penn Plax). A male luer to 3/16" barb connector (NC0465338, Fisher Scientific) was used to connect to a 20 gauge luer stub adapter (22-044086 Fisher Scientific). PE90 tubing was then used to deliver vacuum to the animal. The PE90 tubing was inserted through a hole drilled in the wall of the 3/4-inch ID gasket (Danco 80787) which was secured to the animal using double sided skin tape. GranuFoam™ sponge (KCI) was placed to fill the open space in the gasket, and a clear adhesive drape was placed over the whole assembly.

VAC/Infusion System Control

VAC infusion sequencing is controlled using an Arduino UNO or compatible microcontroller board. Serial ports found on the VAC system and infusion pump were used to synchronize the timing of infusion. The control code was set up for a 5 minute VAC on cycle, so the code would need to be modified and uploaded to the board to utilize a different on cycle timing. The off cycle time does not matter to the current code since the cycle reset is determined by when the VAC turns on according to the serial port output. To properly synchronize the Arduino to the VAC, power on or press the reset button on the Arduino at the same time the VAC first turns on (within about 5 seconds). Infusion started within 15 seconds of the VAC on cycle ending, and lasted for 20 seconds. The infusion rate can then be set based on the rate setting on the infusion pump, along with the appropriate diameter setting based on the syringe size used.

Figure 2B:
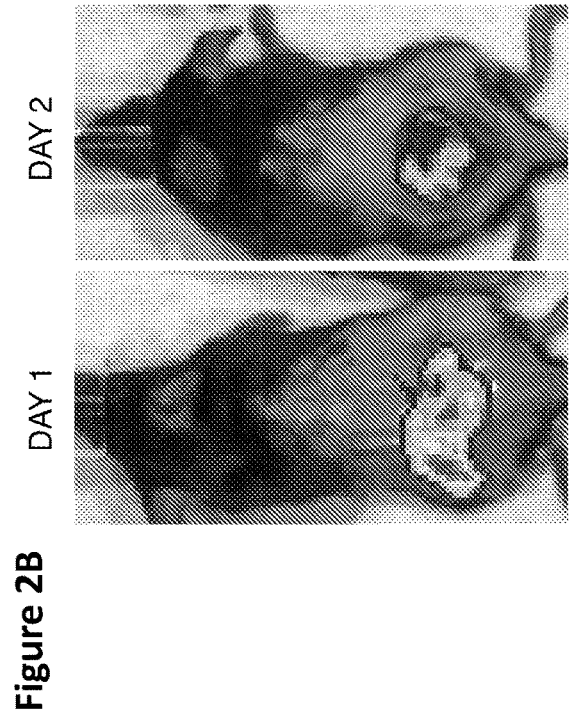
FIG. 2B is a scanning image of a mouse treated with a chemoeffector treatment of this disclosure.
Figure 2B:
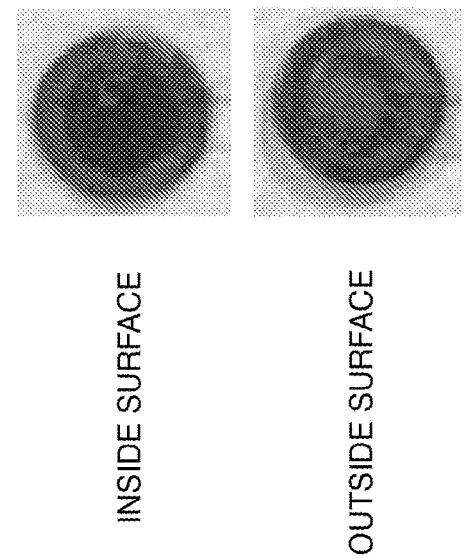
Figure 2A:
FIG. 2A is a scanning image of a mouse treated with control treatment for a wound.
Figure 2A:
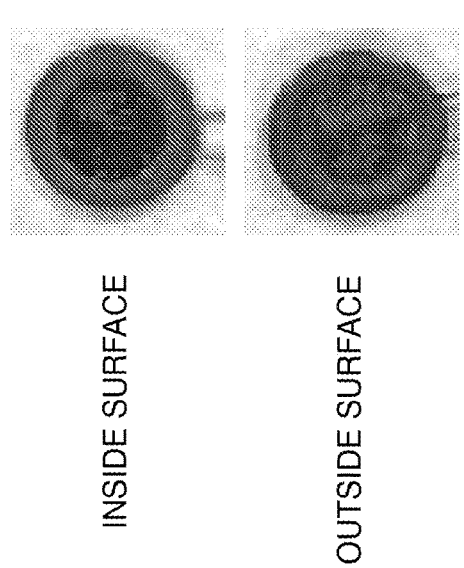

FIGS. 2A and 2B are IVIS Spectrum images of an exemplary control mouse (FIG. 2A; saline infusion to wound packing material) and treatment mouse (FIG. 2B; amino acid cocktail) wound on two days. Image of the sponge (inside and outside surface) is shown below the image of the animal's wound. The calculated relative bacterial burden is shown below the images of the sponge. Imaging shows the relative total bacterial burden is substantially decreased in the treated animal (FIG. 2B).

Figure 3:
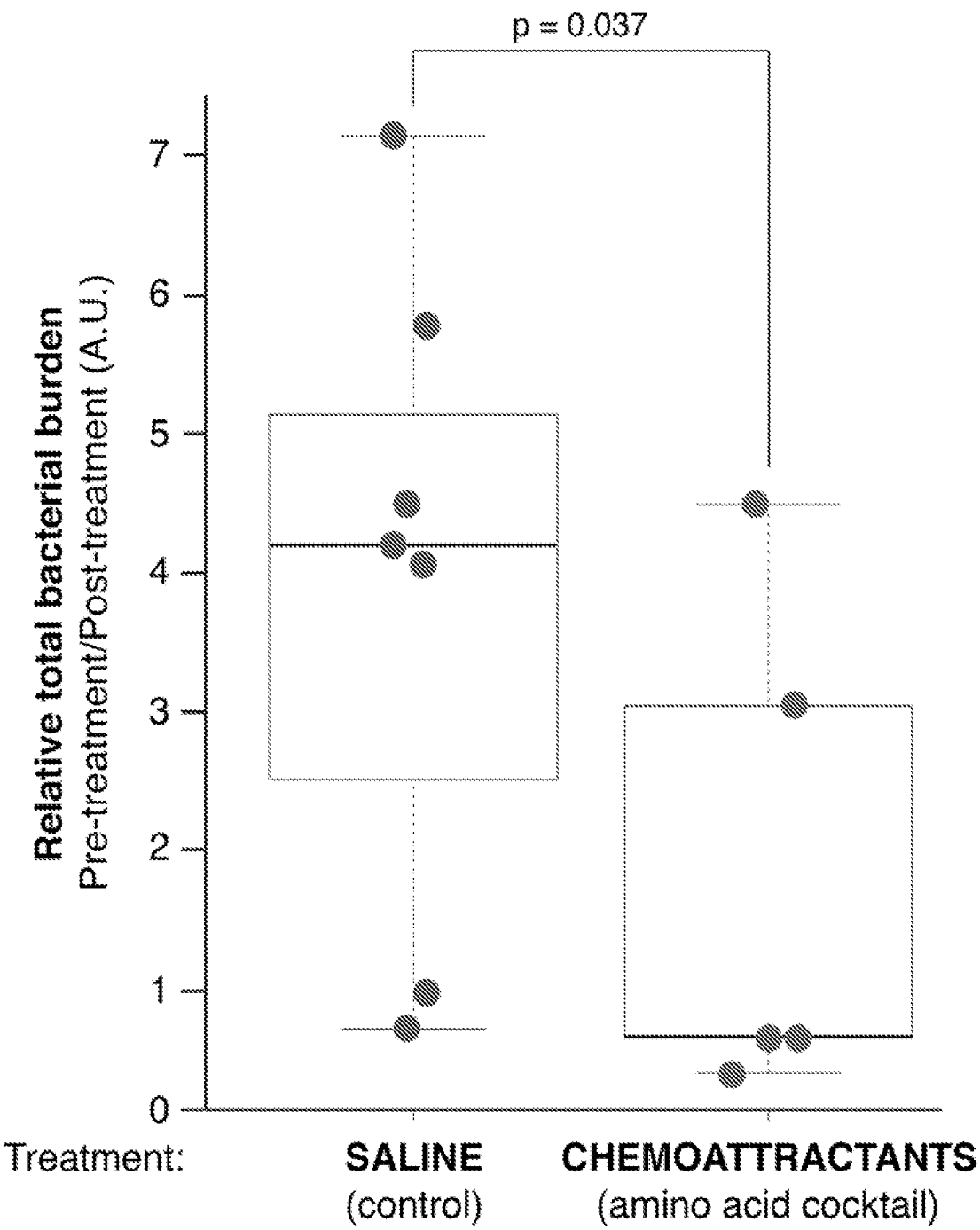
FIG. 3 shows the results of the animal studies comparing the control treatment for the wounds and the chemoeffector treatment for the wounds.

FIG. 3 shows a compilation of the in vivo results. The graph depicts the ratio of bacterial burden post-treatment/pre-treatment of C57 mice infected with *Pseudomonas* and assigned to treatment with a chemoattractant, or saline control, in the wound dressing. The reduction in wound bacterial burden achieved with the added chemoattractant therapy was statistically significant when compared to controls (p=0.037) indicating that this therapy with a chemoattractant cocktail designed to attract *P. aeruginosa* reduced wound bacterial burden to a greater degree than saline controls by quickly reducing the wound bacterial burden via directed chemotaxis. These effects were seen in the absence of antibiotics. Thus, during this therapy, the bacteria were not subjected to selective pressure that can lead to antibiotic resistance.

Example 5

A list of exemplary chemoattractants and/or Binding by Organism in Addition to Optimal pH, Temperature, and Oxygen where Applicable

*Acinetobacter* spp (Displays Motility as Coordinated Biofilm):
1. Drug-resistant strains bind human salivary mucins
2. Motility and formation of biofilms and pellicles were observed only when bacterial cells were incubated in darkness
3. Preferentially adheres to medical tubing and similar surfaces (catheters and ventilator tubing)
4. N-(3-hydroxydodecanoyl)-L-homoserine lactone (3-OH-C12-HSL); C16H29NO4
5. N-Dodecanoyl-L-homoserine lactone (Unsubstituted C-12-HSL); C16H29NO3
6. N-Dodecanoyl-L-homoserine lactone (unsubstituted C-10-HSL); C14H25NO3
7. N-Tetradecanoyl-L-homoserine lactone (unsaturated C-14-HSL); C18H33NO3
8. N-(3-Oxotridecanoyl)-L-homoserine lactone (unsaturated 3-oxo-C13-HSL); C17H29NO4
9. N-Hexanoyldecanoyl-L-homoserine lactone (unsaturated C-16-HSL); C20H35NO3

*Burkholdaria Cepacia*:
1. 2,4,6-trinitrotoluene (TNT)
2. 2,3-DNT, 2,4-DNT
3. 2,5-DNT
4. 2-nitrotoluene (NT)
5. 4NT
6. 4-methyl-5-nitrocatechol (4M5NC)

*Campylobacter Jejuni*:
Chemoattractants
1. *C. jejuni* toward AI-2.
2. Isoleucine
3. Purine
4. Malic acid
5. Fumaric acid
6. Galactose
7. Fucose Chemorepellents
1. Lysine
2. Glucosamine
3. Succinic acid
4. Arginine
5. Thiamine

*Entamoeba Histolytica* (Protozoan):
1. Axenic culture medium (TYI-S)
2. Enzymatic hydrolysate of casein (Trypticase)
3. Partially purified preparation of N-acetylneuraminic acid from egg mucin
4. Amoebae migrated most dramatically toward suspensions of all of seven bacterial species tested, including motile and non-motile, gram-negative and gram-positive rods and cocci

*Enterobacteria*:
1. L-aspartate—high ligand specificity—(at around 5 μM)
2. L-serine—high ligand specificity
3. Human intestinal mucus proteins
4. Canine intestinal mucus proteins
5. Porcine intestinal mucus proteins

*Enterobacteriaceae*:
Chemoattrcatant: Chimerin

*Enterococcus Faecalis*:
Biofilm Formation promoted by:
1. Tryptic Soy Broth
2. Yeast Extract
3. Hemen
4. Vitamin K

*Escherichia Coli*:
Attractants:
1. Quorum sensing autoinducer 2 (AI-2) chemoattractant for enterohemorrhagic *E. coli*
2. *E. coli* toward L-aspartate
3. α-Methyl-DL-aspartate (AMA); Tar receptor mediated; non-natural attractant
4. (±)-α-Amino-3-hydroxy-5-methyl-4-isoxazolepropionic acid (AMPA); Tar receptor mediated; non-natural attractant
5. Formimino-L-aspartate (FIA); Tar receptor mediated; non-natural attractant
6. Guanidinosuccinic acid (GSA); Tar receptor mediated; non-natural attractant
7. N-methyl-L-aspartate (NMA); Tar receptor mediated; non-natural attractant
8. N-formyl-L-aspartate (NFA); Tar receptor mediated; non-natural attractant
9. (2-Imino-4-oxo-thiazolidin-5-yl)-acetic acid (IOTA); Tar receptor mediated; non-natural attractant
10. cis-1,2-cyclohexane-dicarboxylic acid (CHDCA); Tar receptor mediated; non-natural attractant
11. Phthalic acid (PA); Tar receptor mediated; non-natural attractant
12. cis-(2R,3S)-2,3-piperidine dicarboxylic acid (cis-PDA); Tar mediated; non-natural attractant
13. L-malic acid (LMA); Tar receptor mediated; non-natural attractant
14. Glucose
15. Aspartate and serine are the most effective attractants, which induce *E. coli* chemotaxis at a concentration of nanomolar range (Tar and Tsr receptor mediated)
16. D-ribose (Trg receptor mediated)
17. D-glucose (Trg receptor mediated)
18. D-galactose (Trg receptor mediated)
19. Maltose (Tar receptor mediated)
20. Dipeptides, for example: Pro-Leu via Tap receptor dipeptide binding protein
21. 3,4-dihydroxymandelic acid via Tsr receptor
22. Pyrimidine; Tap receptor mediated
23. Thymine; Tap receptor mediated
24. Uracil; Tap receptor mediated
25. Multivalent galactose derivatives via Trg chemoreceptor cluster
26. Multivalent leucine ligands
27. *E coli* will move via pH taxis to areas of neutral acidity
28. *E. coli* chemotaxes toward Ribose and D-ribose via Trg receptor pathway 29. L-arabinose
30. L-sorbose
Repellents:
1. Leucine; via Tsr chemoreceptor
2. Tryptophan; via Tsr chemoreceptor
3. Valine; via Tsr chemoreceptor
4. Phenylalanine; via Tsr chemoreceptor
5. Indole; via Tsr chemoreceptor
6. Glycerol; via Tsr chemoreceptor
*Helicobacter Pylori:*
Chemoattractants
1. *H. pylori* toward AI-2
2. Zymosan activated serum (source of C5a)
3. *H. pylori* supernates)
*Klebsiella Pneumonia* (Biofilm):
1. L-sorbose
Biofilm Formation Inhibited by
1. 5-aminolevulinic acid (5-ALA)
2. 5-ALA methyl ester (MAL)
*Borrelia Burgdorferi:*
Chemoattractants
1. Glucosamine
2. chitosan dimers
3. glutamate
4. N-acetyl-glucosamine
*Listeria Monocytogenes:*
1. Tryptose
2. Glucose
*Mycobacterium Tuberculosis:*
*M. tuberculosis* employs the asparagine transporter AnsP2 and the secreted asparaginase AnsA to assimilate nitrogen and resist acid stress through asparagine hydrolysis and ammonia release. While the role of AnsP2 is partially spared by yet to be identified transporter(s), that of AnsA is crucial in both phagosome acidification arrest and intracellular replication, as an *M. tuberculosis* mutant lacking this asparaginase is ultimately attenuated in macrophages and in mice.
1. Aspariginase
2. Human Nasal Mucin
*Pseudomonas Aeruginosa:*
The bases of amino acid chemotaxis in *P. aeruginosa* are uniquely different than enterobacteria.
1. Strongly attracted to all 20 L-amino acids.
2. Intermediates of amino acid metabolism: putrescine, cadaverine, and gamma-aminobutyrate (GABA), with high specificity being shown for GABA.
3. Repelled by chlorinated contaminants: trichloroethylene, chloroform.
4. Can use L-Gln, GABA, succinate, and glucose as sole carbon source.
5. MUC1 on human airway epithelial cells.
6. Chemotaxes toward the sugars L-fucose, D-galactose, N-acetyl-D-galactosamine, and N-acetyl-D-glucosamine.
7. Porcine gastric mucin.
*Porphyromonas Gingivalis*
1. Cellobiose
2. Fructose
3. Glucose
4. Sucrose
5. Mannitol
*Serratia Marcescens:*
1. l-aspartate
*Staphylococcus Aureus* (CA MRSA, MRSA MSSA) Coordinated Biofilms:
1. Both coagulase negative and coagulase positive staphylococcal tested isolates adhere to the same classes of mammalian cell surface receptors such as mucin-like, fibrinogen-like, fibronectin-like and GAG-like receptors. However, the tested isolates exhibited different degrees of affinities to such receptors.
2. *S. aureus* bind ferret airway mucus
3. *S. aureus* bind human respiratory tract glycolipids
4. *S. aureus* shows strong binding to purified human nasal mucin (purification strategy)
5. *S. aureus* teichoic acids on the cell surface of *S. aureus* have a role in the spreading ability of this bacterium.
*Staphylococcus Epidermidis* Biofilms:
Both coagulase negative and coagulase positive staphylococcal tested isolates adhere to the same classes of mammalian cell surface receptors such as mucin-like, fibrinogen-like, fibronectin-like and GAG-like receptors. However, the tested isolates exhibited different degrees of affinities to such receptors
*Staphylococcus Lugdunensis* Biofilms:
1. polymeric β-1,6-N-acetyl-D-glucosamine (poly-β-1,6-GlcNAc), is required for biofilm formation
*Staphylococcus Saprophyticus* biofilms:
*Streptococcus agalactiae* (binding proteins):
*Streptococcus pyogenes* (binding proteins):
*Vibrio* spp:
1. *Vibrio* spp chemotax toward chitin oligosaccharides
Mucin Subtypes:
Human Mucins: Intestine
1. Mucin Type 0-glycans (oligomeric mucins, aka complex O-linked glycoproteins) as sub-family with common core
2. Secretory gel-forming mucins including MUC2, MUC5AC, MUC5B, MUC6
3. Secretory non gel-forming: MUC7
4. Membrane bound mucins: MUC1, MUC3, MUC4, MUC12, MUC13, MUC17
5. Human Milk Oligosaccharides (HMO's)
Human Mucins: Nasal
1. MUC5AC and MUC5B
Animal Derived Mucins and Other Chemoattractants:
1. Bovine Platelet Factor 4 (bPF4)
2. Canine derived mucin protein
3. Porcine derived intestinal and gastric mucin
4. Bovine sub-maxillary mucin
5. *S. aureus* bind ferret airway mucus
6. *S. aureus* bind bovine submaxillary mucin
7. *Enterobacteria* toward canine intestinal mucus
8. *Enterobacteria* toward porcine intestinal mucus
Sugars and Organic Sugars which Function as Bacterial Chemoattractants:
1. Galactose
2. Glucose
3. Mannose
4. Aspartate, 1-aspartate
6. Ribose and D-ribose
7. L-arabinose
8. Tryptose
9. L-sorbose
pH Taxis:
*E coli* chemotaxis toward neutral pH environment [8]
Miscellaneous Chemoattractant Additives to Foam Environment:
1. Human polymorphonuclear cells (aka neutrophils, or PMNs) chemotax toward bacterial LPS (lipopolysaccharide)
2. Human PMNs chemotax toward bacterial chemotaxin
3. Small metal beads to match metals used in human surgical implants 4. Synthetic surgical meshes used in general and gynecologic surgery
5. Antibiotic binding proteins/resins designed to lower the antibiotic concentration in the sponge environment
6. Multiple human cancer cell lines perform chemotaxis toward oxygen Endogenous Human Chemoattractants
Human Chemokines and Fusokines
Fusokine: chemotactic proteins formed by the fusion of two chemokines
Name/Official Symbol/Conventional Name(s)
CCL Chemokines:
1. CCL1, CCL1, TCA3; I-309
2. CCL2, CCL2, MCP-1; MCAF; JE
3. CCL3, CCL3, MIP-1α; LD78α
4. CCL3L1, CCL3L1, LD78β
5. CCL3P1, CCL3L2, NOT ASSIGNED
6. CCL3L3, CCL3L3, LD78β
7. CCL4, CCL4, MIP-1β
8. CCL4L1, CCL4L1, LAG-1
9. CCL4L2, CCL4L2, LAG-1
10. CCL5, CCL5, RANTES
11. CCL7, CCL7, MCP-3; MARC
12. CCL8, CCL8, MCP-2
13. CCL11, CCL11, Eotaxin
14. CCL13, CCL13, MCP-4
15. CCL14, CCL14, HCC-1
16. CCl15, CCL15, HCC-2
17. CCL16, CCL16, HCC-4; LEC
18. CCL17, CCL17, TARC; ABCD-2
19. CCL18, CCL18, DC-CK-1; PARC; AMAC-1
20. CCL19, CCL19, MIP-3β; ELC; Exodus-3
21. CCL20, CCL20, MIP-3α; LARC; Exodus-1
22. CCL21, CCL21, 6Ckine; SLC; Exodus-2
23. CCL22, CCL22, MDC; STOP-1; AMCD-1
24. CCL23, CCL23, CKβ8; MPIF-1
25. CCL24, CCL24, Eotaxin-2; MPIF-2
26. CCL25, CCL25, TECK
27. CCL26, CCL26, Eotaxin-3, MIP-4α, IMAC
28. CCL27, CCL27, CTACK; ILC; ESKINE
29. CCL28, CCL28, MEC
CXC Chemokines:
30. CXCL1, CXCL1, GRO-α; MGSA-α; MIP-2; KC
31. p-CXCL1, CXCL1P, NOT ASSIGNED
32. CXCL2, CXCL2, GRO-β; MGSA-β; MIP-2α
33. CXCL3, CXCL3, GRO-γ, MGSA-γ; MIP-2β
34. CXCL4, PF4, PF4
35. CXCL4L1, PF4V1, PF4-ALT; CXCL4V1
36. CXCL5, CXCL5, ENA-78
37. CXCL6, CXCL6, GCP-2
38. CXCL7, PPBP, NAP-2; beta-TG; CTAP-III
39. p-CXCL7, PPBPL1, NOT ASSIGNED
40. CXCL8, IL-8, IL-8
41. CXCL9, CXCL9, MIG
42. CXC:10, CXCL10, IP10; CRG-2
43. CXCL11, CXCL11, I-TAC
44. CXCL12, CXCL12, SDF-1α
45. CXCL12, CXCL12, SDF-1β
46. CXCL12, CXCL12, SDF-1γ
47. CXCL13, CXCL13, BCA-1; BLC
48. CXCL14, CXCL14, BRAK
49. CXCL16, CXCL16, SR-PSOX
50. CXCL17, CXCL17, DMC
XC Cytokines:
51. XCL1, XCL1, Lymphotactin; SCM-1α; ATAC
52. XCL2, XCL2, SCM-1β.
CX3C Cytokines:
53. CX3CL1, CX3CL1, Fractalkine; Neurotactin; ABCD-3
Not Assigned:
54. MIF, MIF, Macrophage migration inhibitory factor, glycosylation-inhibiting factor
Human Milk Oligosaccharides:
1. 656 Hex2Sia1
2. 657 Hex2Fuc2
3. 730 Hex3HexNAc1
4. 876 Hex3HexNAc1Fuc1
5. 1022 Hex3HexNAc1Fuc2
6. 1095 Hex4HexNAc2
7. 1241 Hex4HexNAc2Fuc1
8. 1387 Hex4HexNAc2Fuc2
9. 1533 Hex4HexNAc2Fuc3
Human Selectins, Adhesion Molecules, and Growth Factors:
1. E-selectin
2. L-selectin
3. P-selectin
4. VCAM1
5. ICAM-1
6. Mucosal vascular cell-adhesion molecule 1 (MADCAM1)
7. The principal neutrophil β2-integrins: CD11a/CD18 (LFA-1) and CD11b/CD18
8. Vascular Endothelial Growth Factor (VEGF)
Human Cancer Cell Chemoattractants:
Studies point to the following conclusions:
 (i) Tumors express chemokine receptors in a nonrandom manner
 (ii) CXCR4 is the most widely expressed chemokine receptor in many different cancers
 (iii) CCR7 is also expressed by many cancers, and is likely to mediate metastasis to the lymph nodes in selected cancers
 (iv) The effects of CXCL12 on CXCR4-bearing tumor cells likely include many other functions (growth, differentiation) besides migration.
Relating to Breast Cancer:
1. Breast cancer cell chemotaxis toward Epidermal Growth Factor (EGF)
2. CXCL12/CXCR4 (ligand/receptor)
3. CCL21/CCR7 (ligand/receptor)
4. ΔNP63α promotes the chemotaxis of breast cancer cells towards the CXCR4 ligand SDF1α, a process implicated in the trafficking of breast cancer cells to sites of metastasis
5. Currently, no targeted therapy exists for triple negative breast cancer (TNBC). Using mouse models and multiphoton intravital imaging, SHP2 has been identified as having crucial effect of on TNBC cell motility in vivo. Further, analysis of TNBC cells revealed that SHP2 also influences cell migration, chemotaxis and invasion in vitro
6. CCL19, CCL22
7. EGF, TGE, betacellulin, HBEGF, amphiregulin and hergulin
8. FGF, IGF1, CSF1
9. Lung extract
10. Bone extract
11. Wave3
12. Cofilin
13. LIM kinase
14. Arp2/3 complex Relating to Ovarian Cancer:
1. CXCL12
2. CCL19, CCL21
3. CSF1
4. FGF Relating to Glioma:
Chemoattractant GPCRs (expressing cells)—Ligand (cell sources)—Major effects on glioma
FPR1 (glioma cells) fMLF (bacteria); Annexin1 (necrotic glioma cells)
CXCR1 (glioma cells) CXCL8 (glioma cells) Invasion
CXCR2 (glioma cells) CXCL8 (glioma cells) Angiogenesis
CXCR3 (glioma cells) CXCL10 (glioma cells);
CXCL9 (glioma cells) Proliferation; Growth
CXCR4 (glioma cells) CXCL12 (glioma cells, stromal cells) Growth; Angiogenesis; Migration
CXCR5 (glioma cells) CXCL13 (glioma cells) CXCR7 (glioma cells)
CXCL12 (glioma cells and stromal cells) Anti-apoptosis
CCR2A (glioma cells) CCL2 (glioma cells) Migration
CCR3 (glioma cells) CCL3L1 (glioma cells) Proliferation
CCR4 (Treg cells) CCL22 (glioma cells) Treg infiltration
CCR5 (glioma cells) CCL3L1 (glioma cells) Proliferation
CX3CR1 (glioma cells and GIMs) CX3CL1 (glioma cells) Tumorigenesis; Pro- or anti-invasion based on whether CX3CL1 is soluble or membrane bound.
GIMs: glioma infiltrating macrophages; Treg: regulatory T cells.

Relating to Colon Cancer:
1. CCR6-CCL20 pathway in human colon cancer metastasis Relating to Cervical Cancer:
1. Th17 cervical cancer cell lines chemotax toward CCL20 via CCR6-CCL20 pathway Relating to Melanoma:
1. CCL5, CCL2, CCL3, CCL7
2. CCL25
3. PDGF
4. IGF1
5. VEGF and VEGFC
6. CXCL12
7. Brain extract
8. WAVE1, WAVE2
9. lysophosphatidic acid (LPA)
10. Growth factors Relating to Pancreatic Cancer:
CCL21 induces chemotaxis of pancreatic cancer cells Relating to Sarcoma:
1. CXCL12
2. FGF
3. IGF1
4. VEGF and VEGFC
5. Lung extract The foregoing examples of the present disclosure have been presented for purposes of illustration and description. Furthermore, these examples are not intended to limit the disclosure to the form disclosed herein. Consequently, variations and modifications commensurate with the teachings of the description of the disclosure, and the skill or knowledge of the relevant art, are within the scope of the present disclosure. The specific embodiments described in the examples provided herein are intended to further explain the best mode known for practicing the disclosure and to enable others skilled in the art to utilize the disclosure in such, or other, embodiments and with various modifications required by the particular applications or uses of the present disclosure. It is intended that the appended claims be construed to include alternative embodiments to the extent permitted by the prior art.

What is claimed is:

1. A wound packing material comprising an open-cell polymer selected from a polyvinyl alcohol (PVA) or polyurethane (PU) admixed with at least one chemoattractant agent that is chemoattractant to a microorganism, wherein the at least one chemoattractant agent is selected from the group consisting of N-(3-hydroxydodecanoyl)-L-homoserine lactone, N-Dodecanoyl-L-homoserine lactone, N-Tetradecanoyl-L-homoserine lactone, N-(3-Oxotridecanoyl)-L-homoserine lactone, N-Hexanoyldecanoyl-L-homoserine lactone, enzymatic hydrolysate of casein (Trypticase), N-acetylneuraminic acid from egg mucin, L-aspartate, human intestinal mucus proteins, canine intestinal mucus proteins, porcine intestinal mucus proteins, quorum sensing autoinducer 2 (AI-2), α-Methyl-DL-aspartate (AMA), (±)-α-Amino-3-hydroxy-5-methyl-4-isoxazolepropionic acid (AMPA), N-methyl-L-aspartate (NMA), (2-Imino-4-oxo-thiazolidin-5-yl)-acetic acid (IOTA), cis-1,2-cyclohexane-dicarboxylic acid (CHDCA), phthalic acid (PA), cis-(2R, 3S)-2,3-piperidine dicarboxylic acid (cis-PDA), L-malic acid (LMA), D-glucose, D-galactose, 3,4-dihydroxymandelic acid, D-ribose, L-arabinose, L-sorbose, tryptose, gamma-aminobutyrate (GABA), L-fucose, D-galactose, ferret airway mucus, human respiratory tract glycolipids, human salivary mucins, human nasal mucin, Mucin Type O-glycans, secretory gel-forming mucins, MUC2, MUC5AC, MUC5B, MUC6, MUC7, MUC1, MUC3, MUC4, MUC12, MUC13, MUC17U, Human Milk Oligosaccharides, bovine submaxillary mucin, bacterial chemotaxin, CCL1, TCA3, 1-309, MCAF, JE, LD78α, CCL3L1, LD78β, CCL3P1, CCL3L2, CCL3L3, LD78β, CCL4, CCL4L1, LAG-1, CCL4L2, LAG-1, MARC, CCL8, CCL11, CCL13, CCL14, HCC-1, CCL15, HCC-2, CCL16, HCC-4, LEC, CCL17, TARC, ABCD-2, CCL18, DC-CK-1, PARC, AMAC-1, Exodus-3, LARC, Exodus-1, 6Ckine, SLC, Exodus-2, MDC, STCP-1, AMCD-1, CCL23, CKβ8, MPIF-1, CCL24, MPIF-2, TECK, CCL26, IMAC, CCL27, CTACK, ILC, ESKINE, CCL28, MEC, CXCL1, GRO-α, MGSA-α, p-CXCL1, CXCL1P, CXCL2, GRO-β, MGSA-β, CXCL3, GRO-γ, MGSA-γ, CXCL4, PF4, CXCL4L1, PF4V1, PF4-ALT, CXCL4V1, CXCL5, ENA-78, CXCL6, GCP-2, PPBP, NAP-2, beta-TG, CTAP-III, p-CXCL7, PPBPL1, CXC:10, IP10, CRG-2, CXCL11, I-TAC, SDF-1α, SDF-1β, SDF-1γ, BCA-1, BLC, CXCL14, CXCL16, SR-PSOX, CXCL17, XCL1, Lymphotactin, SCM-1α, ATAC, XCL2, SCM-1β, Fractalkine, Neurotactin, ABCD-3, MIF, Macrophage migration inhibitory factor, glycosylation-inhibiting factor, 656 Hex2Sia1, 657 Hex2Fuc2, 730 Hex3HexNAc1, 876 Hex3HexNAc1Fuc1, 1022 Hex3HexNAc1Fuc2, 1095 Hex4HexNAc2, 1241 Hex4HexNAc2Fuc1, 1387 Hex4HexNAc2Fuc2, 1533 Hex4HexNAc2Fuc3, E-selectin, L-selectin, P-selectin, VCAM1, ICAM-1, Mucosal vascular cell-adhesion molecule 1 (MADCAM1), neutrophil β2-integrins (CD11a/CD18 (LFA-1) and CD11b/CD18), and combinations thereof.

2. The wound packing material of claim 1, wherein the wound packing material comprises a foam.

3. The wound packing material of claim 1, wherein the wound packing material comprises a gauze.

4. A wound dressing for use in negative pressure wound therapy, the wound dressing comprising an occlusive backing layer fitted with a drainage port, and a wound packing material of claim 1.

5. A kit comprising:
a wound packing material as set forth in claim 1;
a cover material for forming a seal over a wound space; and,
connection for a negative pressure source.

6. A kit of claim 5, wherein the kit is provided in a water-proof pack and in a sterile form.

7. A kit of claim 5, wherein a pack containing the kit components is provided in a form whereby radiation and/or ethylene oxide can be used for sterilization.

8. A kit of claim 5, further comprising at least one of an adhesive to fix wound dressings, an air-tight seal of wound dressings, a pressure sensor, a connection element for a pressure sensor, a disinfectant, a skin care product, instructions for use, scissors, pads and pincers.

9. The wound packing material of claim 1, wherein the chemoattractant agent is chemoattractant to a human cell infected with a virus.

10. The wound packing material of claim 1, wherein the chemoattractant agent is chemoattractant to a bacteria.

11. The wound packing material of claim 1, wherein the chemoattractant agent is chemoattractant to a at least one microorganism selected from the group consisting of: *Acinetobacter* spp, *Burkholdaria cepacia*, *Campylobacter jejuni*, *Candida albicans* (binding proteins), *Candida glabrata* (binding proteins), *Entamoeba histolytica* (protozoan), *Plasmodium* spp (protozoan), *Enterobacteria*, *Enterococcus* (VRE), *Escherichia coli*, *Helicobacter pylori*, *Klebsiella pneumonia*, *Listeria monocytogenes*, Mucormycosis, *Mycobacterium tuberculosis*, *Pasteurella* spp, *Propionibacterium acnes*, *Proteus mirabilis*, *Pseudomonas aeruginosa*, *Salmonella typhi*, paratyphi, *Serratia marcescens* and other *Serratia* spp, *Shigella* spp (*dysenteriae*, *flexneri*, *boydii*, *sonnei*), *Staphylococcus aureus* (CA MRSA, MRSA MSSA) biofilms, *Staphylococcus epidermidis*, *Staphylococcus lugdunensis*, *Staphylococcus saprophyticus*, *Streptococcus agalactiae*, *Streptococcus pneumonia*, *Streptococcus pyogenes*, and *Vibrio* spp.

12. The wound packing material of claim 1, wherein the wound packing material does not comprise an antibiotic.

13. The wound packing material of claim 1, wherein the wound packing material does not comprise an antimicrobial.

14. The wound packing material of claim 12, wherein the pH of the wound packing material is between about pH 6 and about pH 8.

15. The wound packing material of claim 1, wherein the chemoattractant agent comprises about 0.01% to about 30% by weight, relative to the total weight of the wound packing material.

* * * * *